US00RE44934E

(19) United States
(12) Reissued Patent
Provan et al.

(10) Patent Number: US RE44,934 E
(45) Date of Reissued Patent: *Jun. 10, 2014

(54) ZIPPER AND ZIPPER ARRANGEMENTS AND METHODS OF MANUFACTURING THE SAME

(75) Inventors: Alexander R. Provan, Wolcott, NY (US); Thomas L. Coomber, Macedon, NY (US); Ian J. Barclay, Marion, NY (US); David V. Dobreski, Canandaigua, NY (US); Toby R. Thomas, Pleasant Prairie, WI (US)

(73) Assignee: Reynolds Presto Products Inc., Appleton, WI (US)

( * ) Notice: This patent is subject to a terminal disclaimer.

(21) Appl. No.: 10/652,572

(22) Filed: Aug. 29, 2003

Related U.S. Patent Documents

Reissue of:
(64) Patent No.: 6,286,189
Issued: Sep. 11, 2001
Appl. No.: 09/307,937
Filed: May 10, 1999

(51) Int. Cl.

| | |
|---|---|
| ***A44B 19/16*** | (2006.01) |
| ***A44B 19/42*** | (2006.01) |
| *B65B 9/08* | (2012.01) |
| *B65D 33/25* | (2006.01) |

(52) U.S. Cl.
USPC ..... 24/30.5 R; 24/400

(58) Field of Classification Search
USPC ..... 24/30.5 R, 399, 400, 30.5 P, 381, 585.1, 24/585.11, 585.12, DIG. 38, DIG. 39, 24/DIG. 40, DIG. 50; 53/412, 139.2, 133.4; 383/5, 203, 204, 207, 208, 210, 210.1, 383/63, 64, 65, 68, 69, 61.2, 61.3; 493/213, 493/214; 156/66
See application file for complete search history.

(56) References Cited

U.S. PATENT DOCUMENTS

| | | | |
|---|---|---|---|
| 1,785,234 | A | 12/1930 | Sundback |
| 2,091,617 | A | 8/1937 | Sundback |

(Continued)

FOREIGN PATENT DOCUMENTS

| | | |
|---|---|---|
| AU | 252779 | 3/1962 |
| AU | 252799 | 9/1963 |

(Continued)

OTHER PUBLICATIONS

European Search Report for Application No. EP 06 00 1558 dated Mar. 17, 2006 (4 pages).

(Continued)

*Primary Examiner* — James Brittain
(74) *Attorney, Agent, or Firm* — Nixon Peabody LLP

(57) ABSTRACT

A zipper arrangement for use in manufacturing thermoplastic bags that includes a zipper and at least one slider. The zipper includes first and second opposing tracks. The first track has a first profile and the second track has a second profile. The first and second profiles are releasably engageable to each other. The first track has one or more spaced primary notches interrupting the first profile. At least one slider is inserted onto the first profile via a respective one of the primary notches. The slider is adapted to engage and disengage the first and second profiles in response to movement along the zipper. The second track may have one or more to spaced primary notches interrupting the second profile. The spaced primary notches of the second track are generally aligned to respective ones of the primary notches of the first track. At least one slider is inserted onto the aligned pairs of primary notches via a respective one of the generally aligned notches.

64 Claims, 7 Drawing Sheets

(56) References Cited

U.S. PATENT DOCUMENTS 2,779,385 A 1/1957 Carlzen et al.
3,074,137 A 1/1963 Hawley
3,149,927 A 9/1964 Fady
3,225,429 A 12/1965 Fady
3,259,951 A 7/1966 Zimmerman
3,381,592 A 5/1968 Ravel
3,394,798 A 7/1968 Sako
3,426,396 A 2/1969 Laguerre
3,473,589 A 10/1969 Gotz
3,532,571 A 10/1970 Ausnit
RE27,174 E 9/1971 Ausnit
3,608,439 A 9/1971 Ausnit
3,613,524 A 10/1971 Behr et al.
3,644,981 A 2/1972 Gustavsson
3,701,191 A 10/1972 Laguerre
3,701,192 A 10/1972 Laguerre
3,736,198 A 5/1973 Leistner
3,785,111 A 1/1974 Pike
3,790,992 A 2/1974 Herz
3,806,988 A 4/1974 Laguerre
3,839,128 A 10/1974 Arai
3,849,843 A 11/1974 Alberts
3,868,891 A 3/1975 Parish
3,948,702 A 4/1976 Ausnit ..... 156/73.4
3,948,705 A 4/1976 Ausnit
3,962,007 A 6/1976 Heimberger
3,991,801 A 11/1976 Ausnit
4,094,729 A 6/1978 Boccia
4,101,355 A 7/1978 Ausnit
4,122,594 A 10/1978 Azzara
4,173,283 A 11/1979 Takamatsu
4,196,030 A 4/1980 Ausnit
4,232,429 A 11/1980 Friedberg
4,241,865 A 12/1980 Ferrell
4,240,241 A 7/1981 Schulze
4,277,241 A 7/1981 Schulze
4,341,575 A 7/1982 Herz
4,355,494 A 10/1982 Tilman
4,372,793 A 2/1983 Herz
4,395,891 A 8/1983 Remington
4,415,386 A 11/1983 Ferrell et al.
RE31,487 E 1/1984 Friedberg
4,430,070 A 2/1984 Ausnit
4,430,071 A 2/1984 Ausnit ..... 493/215
4,437,293 A 3/1984 Sanborn, Jr.
4,446,088 A 5/1984 Daines
4,517,788 A 5/1985 Scheffers
4,528,224 A 7/1985 Ausnit
4,563,319 A 1/1986 Ausnit et al.
4,581,006 A 4/1986 Hugues et al.
4,582,549 A 4/1986 Ferrell
4,601,694 A 7/1986 Ausnit
4,612,153 A 9/1986 Mangla
4,617,683 A 10/1986 Christoff
4,620,320 A 10/1986 Sullivan
4,637,063 A 1/1987 Sullivan et al.
4,651,504 A 3/1987 Bentsen
4,655,862 A 4/1987 Christoff et al.
4,663,915 A 5/1987 Van Erden et al.
4,666,536 A 5/1987 Van Erden et al.
4,673,383 A 6/1987 Bentsen
4,691,372 A 9/1987 Van Erden
4,703,518 A 10/1987 Ausnit
4,709,398 A 11/1987 Ausnit
4,709,533 A 12/1987 Aunit
4,710,157 A 12/1987 Posey
4,745,731 A 5/1988 Talbott et al.
4,756,629 A 7/1988 Tilman et al.
4,782,951 A 11/1988 Griesbach et al.
4,786,190 A 11/1988 Van Erden et al.
4,787,880 A 11/1988 Ausnit
4,790,126 A 12/1988 Boeckmann
4,792,240 A 12/1988 Ausnit
4,807,300 A 2/1989 Ausnit et al.
4,812,074 A 3/1989 Ausnit et al.
4,832,505 A 5/1989 Ausnit et al.
4,840,012 A 6/1989 Boeckmann
4,840,611 A 6/1989 Van Erden et al.
4,844,759 A 7/1989 Boeckmann
4,850,178 A 7/1989 Ausnit
4,863,285 A 9/1989 Claxton
4,876,842 A 10/1989 Ausnit
4,878,987 A 11/1989 Van Erden
4,891,867 A 1/1990 Takeshima et al.
4,892,414 A 1/1990 Ausnit
4,892,512 A 1/1990 Branson
4,894,975 A 1/1990 Ausnit
4,909,017 A 3/1990 McMahon et al.
4,924,655 A 5/1990 Posey
4,925,316 A 5/1990 Van Erden et al.
4,925,318 A 5/1990 Sorensen
4,929,225 A 5/1990 Ausnit et al.
4,941,307 A 7/1990 Wojcik
4,969,309 A 11/1990 Schwarz et al.
4,971,454 A 11/1990 Branson et al.
4,974,395 A 12/1990 McMahon
4,987,658 A 1/1991 Horita
4,993,212 A 2/1991 Veoukas
5,005,707 A 4/1991 Hustad et al.
5,010,627 A 4/1991 Herrington et al.
5,014,498 A 5/1991 McMahon
5,024,537 A 6/1991 Tilman
5,027,584 A 7/1991 McMahon et al.
5,036,643 A 8/1991 Bodolay
5,042,224 A 8/1991 McMahon
5,046,300 A 9/1991 Custer et al.
5,063,639 A 11/1991 Boeckmann et al.
5,063,644 A 11/1991 Herrington et al.
5,067,208 A 11/1991 Herrington, Jr. et al.
5,067,822 A 11/1991 Wirth et al.
5,071,689 A 12/1991 Tilman
5,072,571 A 12/1991 Boeckmann
5,085,031 A 2/1992 McDonald
5,088,971 A 2/1992 Herrington
5,092,831 A 3/1992 James et al.
5,096,516 A 3/1992 McDonald et al.
5,105,603 A 4/1992 Natterer
5,107,658 A 4/1992 Hustad et al.
5,111,643 A 5/1992 Hobock
5,116,301 A 5/1992 Robinson et al.
5,127,208 A 7/1992 Custer et al.
5,131,121 A 7/1992 Herrington, Jr. et al.
5,147,272 A 9/1992 Richison et al.
5,157,811 A 10/1992 Bodolay
5,161,286 A 11/1992 Herrington, Jr. et al.
5,167,608 A 12/1992 Steffens, Jr. et al.
5,179,816 A 1/1993 Wojnicki
5,188,461 A 2/1993 Sorenson
5,198,055 A 3/1993 Wirth et al.
5,211,482 A 5/1993 Tilman
5,247,781 A 9/1993 Runge
5,254,073 A 10/1993 Richison et al.
5,259,904 A 11/1993 Ausnit
5,273,511 A 12/1993 Boeckman
RE34,554 E 3/1994 Ausnit
5,301,395 A 4/1994 Richardson et al.
5,322,579 A 6/1994 van Erden
5,334,127 A 8/1994 Bruno et al.
5,383,989 A 1/1995 McMahon
5,391,136 A 2/1995 Makowa
5,400,565 A 3/1995 Terminella et al.
5,400,568 A 3/1995 Kanemitsu et al.
RE34,905 E 4/1995 Ausnit
5,403,094 A 4/1995 Tomic
5,405,478 A 4/1995 Richardson et al.
5,405,629 A 4/1995 Marnocha et al.
5,412,924 A 5/1995 Ausnit
5,415,904 A 5/1995 Takubo et al.
5,425,216 A 6/1995 Ausnit
5,425,825 A 6/1995 Rasko et al.
5,431,760 A 7/1995 Donovan
5,435,864 A 7/1995 Machacek et al.
5,442,837 A 8/1995 Morgan
5,448,807 A 9/1995 Herrington, Jr.

(56) References Cited

U.S. PATENT DOCUMENTS

| | | | |
|---|---|---|---|
| 5,456,928 | A | 10/1995 | Hustad et al. |
| 5,461,845 | A | 10/1995 | Yeager |
| 5,470,156 | A | 11/1995 | May |
| 5,482,375 | A | 1/1996 | Richardson et al. |
| 5,486,051 | A | 1/1996 | May |
| 5,489,252 | A | 2/1996 | May |
| 5,492,411 | A | 2/1996 | May |
| 5,505,037 | A | 4/1996 | Terminella et al. |
| 5,509,735 | A | 4/1996 | May |
| 5,511,884 | A | 4/1996 | Bruno et al. |
| 5,513,915 | A | 5/1996 | May |
| 5,519,982 | A | 5/1996 | Herber et al. |
| 5,525,363 | A | 6/1996 | Herber et al. |
| 5,542,902 | A | 8/1996 | Richison et al. |
| 5,551,127 | A | 9/1996 | May |
| 5,551,208 | A | 9/1996 | Van Erden |
| 5,552,202 | A | 9/1996 | May |
| 5,557,907 | A | 9/1996 | Malin et al. |
| 5,558,613 | A | 9/1996 | Tilman et al. |
| 5,561,966 | A | 10/1996 | English |
| 5,564,259 | A | 10/1996 | Stolmeier |
| 5,573,614 | A | 11/1996 | Tilman et al. |
| 5,582,853 | A | 12/1996 | Marnocha et al. |
| 5,592,802 | A | 1/1997 | Malin et al. |
| 5,613,934 | A | 3/1997 | May |
| 5,622,431 | A | 4/1997 | Simonsen |
| 5,628,566 | A | 5/1997 | Schreiter |
| 5,647,671 | A | 7/1997 | May |
| 5,664,296 | A | 9/1997 | May |
| 5,669,715 | A | 9/1997 | Dobreski et al. |
| 5,682,730 | A | 11/1997 | Dobreski |
| 5,711,751 | A | 1/1998 | Harmanoglu |
| 5,713,110 | A | 2/1998 | Covi et al. |
| 5,713,669 | A | 2/1998 | Thomas et al. |
| 5,725,312 | A | 3/1998 | May |
| 5,745,960 | A | 5/1998 | Dishner et al. |
| 5,749,134 | A | 5/1998 | Zemitis |
| 5,782,733 | A | 7/1998 | Yeager |
| 5,788,378 | A | 8/1998 | Thomas |
| 5,823,933 | A | 10/1998 | Yeager |
| 5,833,791 | A | 11/1998 | Bryniarski et al. |
| 5,851,070 | A | 12/1998 | Dobreski et al. |
| 5,871,281 | A | 2/1999 | Stolmeier et al. |
| 5,896,627 | A | 4/1999 | Cappel et al. |
| 5,906,438 | A | 5/1999 | Laudenberg |
| 5,924,173 | A | 7/1999 | Dobreski et al. |
| 5,938,337 | A | 8/1999 | Provan et al. |
| 5,953,796 | A | 9/1999 | McMahon et al. |
| 5,956,815 | A | 9/1999 | O'Connor et al. |
| 5,956,924 | A | 9/1999 | Thieman |
| 5,964,532 | A | 10/1999 | St. Phillips et al. |
| 6,138,436 | A | 10/2000 | Malin et al. |
| 6,138,439 | A | 10/2000 | McMahon et al. |
| 6,178,722 | B1 | 1/2001 | McMahon |
| 6,209,287 | B1 | 4/2001 | Thieman |
| 6,212,857 | B1 | 4/2001 | Van Erden |
| 6,216,423 | B1 | 4/2001 | Thieman |
| 6,292,986 | B1 | 9/2001 | Provan et al. |
| 6,327,754 | B1 | 12/2001 | Belmont et al. |
| 6,360,513 | B1 | 3/2002 | Strand et al. |
| 6,363,692 | B2 | 4/2002 | Thieman |
| 6,412,254 | B1 | 7/2002 | Tilman et al. |
| 6,438,926 | B1 | 8/2002 | Thieman |
| 6,499,272 | B2 | 12/2002 | Thieman |
| 2002/0194818 | A1 | 12/2002 | Thieman |
| 2003/0074861 | A1 | 4/2003 | Thieman |
| 2003/0220179 | A1 | 11/2003 | Thieman |
| 2003/0220180 | A1 | 11/2003 | Thieman |
| 2004/0000124 | A1 | 1/2004 | Thieman |
| 2004/0074058 | A1 | 4/2004 | Thieman |

FOREIGN PATENT DOCUMENTS

| | | | | |
|---|---|---|---|---|
| CA | 2 274 134 | A1 | 6/1998 | ..... A44B 19/16 |
| DE | 2053550 | | 5/1972 | |
| EM | 0 051 010 | A1 | 5/1982 | ..... A44B 19/62 |
| EM | 0 275 396 | A1 | 7/1988 | ..... B65B 61/18 |
| EM | 0 505 059 | A1 | 9/1992 | ..... A44B 19/26 |
| EM | 0 978 450 | | 2/2000 | |
| EP | 0 505 055 | | 9/1992 | |
| EP | 0 761 532 | | 8/1996 | |
| EP | 0 978 450 | A1 | 2/2000 | ..... B65B 9/20 |
| FR | 1 564 039 | | 3/1969 | |
| FR | 2 126 060 | | 10/1972 | ..... A44B 19/00 |
| FR | 2 546 481 | A1 | 11/1984 | ..... B65D 33/24 |
| FR | 2 716 158 | B1 | 5/1996 | ..... B65B 9/12 |
| FR | 2 773 679 | A1 | 1/1998 | |
| GB | 0522663 | | 6/1940 | |
| GB | 1173019 | | 12/1969 | |
| GB | 2 085 519 | A1 | 4/1982 | ..... A44B 19/62 |
| GB | 2085519 | | 4/1982 | |
| GB | 2085519 | A | 4/1982 | ..... A44B 19/62 |
| GB | 2 109 771 | | 6/1983 | |
| GB | 2138494 | | 10/1984 | |
| WO | 89/03345 | A1 | 4/1989 | ..... B65B 9/06 |
| WO | WO 98/05567 | | 2/1998 | |
| WO | 98/24339 | A1 | 6/1998 | ..... A44B 19/16 |
| WO | WO 99/03672 | | 1/1999 | |
| WO | 99/24325 | | 5/1999 | |

OTHER PUBLICATIONS

Extended European Search Report for Application No. EP 06 016 369.8 dated Sep. 20, 2006 (5 pages).

European Search Report for Application No. EP 0402 2558 dated Oct. 21, 2004 (5 pages).

Extended European Search Report for Application No. EP 06 01 6376 dated Oct. 13, 2006 (4 pages).

Notice of Opposition to European Patent EP 1 714 574, dated Aug. 27, 2008, 14 pages.

Response to Opposition to European Patent EP 1 715 574 filed with European Patent Office on Sep. 27, 2008, dated Feb. 11, 2009, 14 pages.

Follow-up Communication from Opposer Concerning Opposition to European Patent EP 1 714 574, dated Jun. 19, 2009, 8 pages.

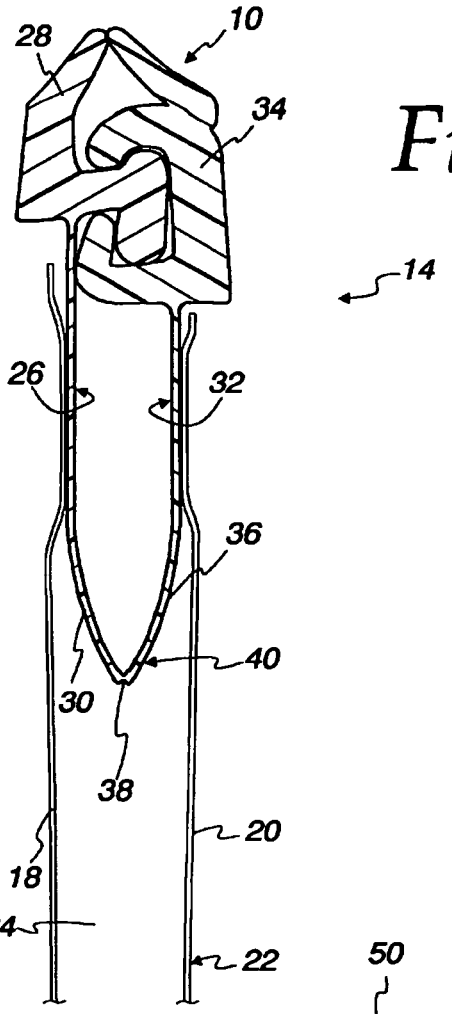
Fig. 3
Fig. 4
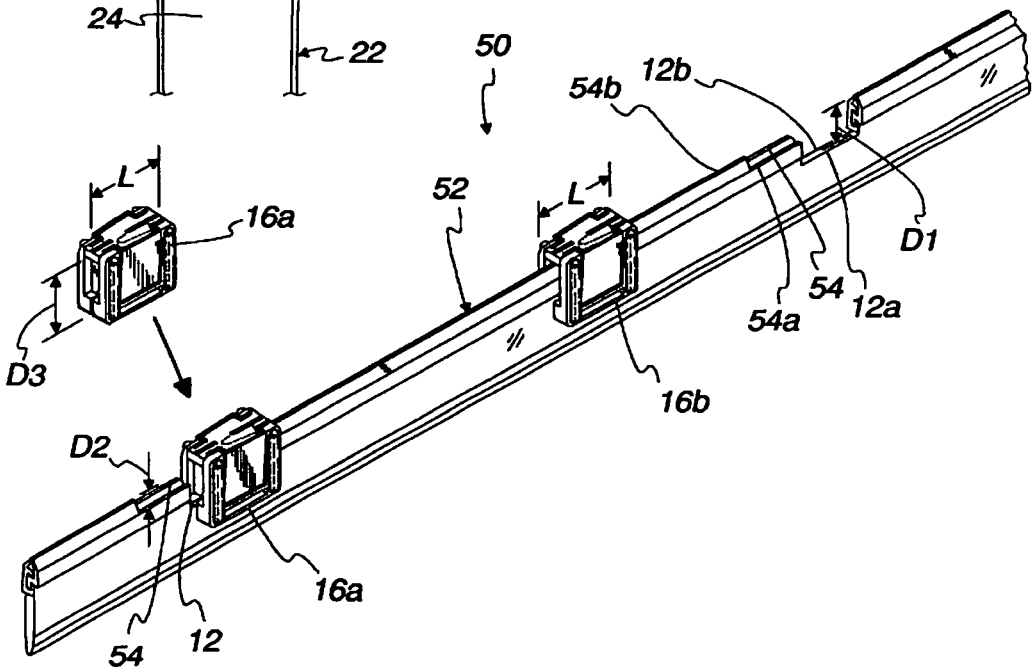

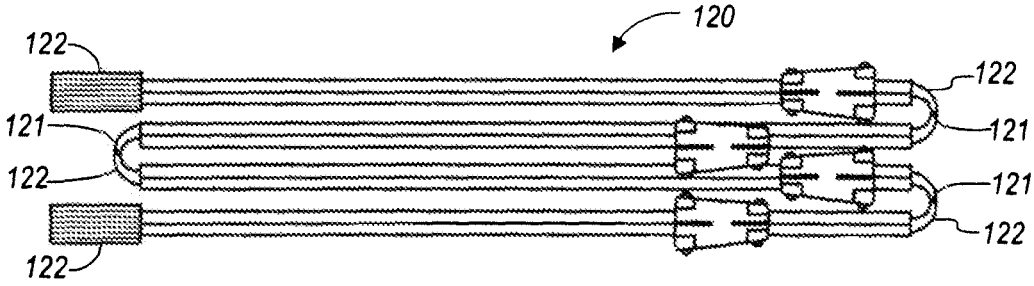
Fig. 7d
NEW

ZIPPER AND ZIPPER ARRANGEMENTS AND METHODS OF MANUFACTURING THE SAME

Matter enclosed in heavy brackets [ ] appears in the original patent but forms no part of this reissue specification; matter printed in italics indicates the additions made by reissue.

RELATED APPLICATIONS

*The Applicants note that application Ser. No. 13/184,010 was filed on Jul. 15, 2011. Application Ser. No. 13/184,010 is a continuation reissue application from this application (application Ser. No. 10/652,572).*

This application *is a reissue application of U.S. Pat. No. 6,286,189 (application Ser. No. 09/307,937); U.S. Pat. No. 6,286,189* is related to an application entitled "Assembly And Accumulation Of Sliders For Profiled Zippers" Ser. No. 09/307,893 filed May 10, 1999, and to an application entitled "Fastener With Slider Thereon For Use In Manufacturing Recloseable Bags" Ser. No. 09/302,843 filed May 10, 1999. Both applications are filed concurrently with this application, and are assigned to the same assignee as the assignee of this application. Both applications and their disclosures are incorporated herein by reference in their entirety.

FIELD OF THE INVENTION

The present invention is directed to zippers, zipper arrangements, and methods of manufacturing the same. Specifically, the present invention is directed towards zipper arrangements having a notched zipper and at least one slider for use in manufacturing thermoplastic bags and methods of manufacturing the same.

BACKGROUND OF THE INVENTION

Plastic bags are popular for storing food and other items. Zippered plastic bags that can be securely closed and reopened are particularly popular due to their perceived ability to maintain freshness of the food stored in the bags and/or to minimize or eliminate leakage into and out of the bag. These bags are used one at a time by consumers. These bags are also used by businesses to package items that are then sold to consumers. For example, nuts, candy, snacks, ingredients, salt, cheese, and other food and non-food products are packed in these bags by form, fill and seal machines.

Slider bags have become popular with customers for a variety of reasons, including difficulty in opening and closing a zippered bag without a slider. Product manufacturers have not, however, used zippers with sliders in their form, fill and seal machines for a variety of reasons. Some of these reasons include the difficulty in having a reliable assembly of sliders to zipper at form, fill and seal manufacturing rates, supplying zipper with sliders that are not prone to machine jamming and excessive downtime, and installing sliders in tight and constraining areas in form, fill and seal machine footprints.

Accordingly, a need exists to address the above-noted problems by supplying zippers in a convenient configuration and having methods of easily placing sliders onto zippers.

SUMMARY OF THE INVENTION

According to one embodiment of the present invention, a zipper arrangement for use in manufacturing bags includes a zipper and at least one slider. The zipper includes first and second opposing tracks. The first track has a first profile and the second track has a second profile. The first and second profiles are releasably engageable to each other. The first track has one or more spaced primary notches interrupting the first profile. The slider is inserted onto the first profile via a respective one of the primary notches. The slider is adapted to engage and disengage the first and second profiles in response to movement along the zipper.

According to another embodiment of the present invention, the second track has a second profile and one or more spaced primary notches interrupting the second profile. The second primary notches are generally aligned with respective ones of the first primary notches to form aligned pairs of primary notches. The slider is inserted onto the first profile via a respective one of the aligned pairs of primary notches.

According to yet another embodiment of the present invention, a folded zipper includes first and second opposing tracks that each have one or more primary notches interrupting respective profiles. The primary notches are generally aligned to respective ones of the first primary notches to form aligned pairs of primary notches. The zipper includes a plurality of fold areas generally transverse to a length of the zipper and the zipper is folded along the fold areas.

According to a further embodiment, a folded zipper has a first track having one or more primary notches and a second track having one or more spaced slits interrupting the second profile. The slits are generally aligned to respective ones of the primary notches. The zipper includes a plurality of fold areas generally transverse to a length of the zipper and the zipper is folded along the fold areas.

According to one method of the present invention, a zipper and at least one slider are provided. The first track has one or more spaced primary notches interrupting the first profile. The slider is mounted onto a second profile and into a respective one of the primary notches. The slider is slid onto the first profile via a respective one the primary notches.

According to another method, a zipper and at least one slider are provided. The slider is positioned in a respective one of the aligned pairs of primary notches. Each of the first and second opposing tracks has one or more primary notches interrupting respective profiles. The slider is slid onto the first and second profiles via a respective one of the aligned pairs of primary notches.

BRIEF DESCRIPTION OF THE DRAWINGS

Other objects and advantages of the invention will become apparent upon reading the flowing detailed description and upon reference to the drawings.

FIG. 3 is a cross-sectional view of the zipper taken across line 3-3 of FIG. 2 prior to opening the tamper evident feature.

FIG. 4 is a perspective view of a zipper arrangement including a zipper and a plurality of sliders according to another embodiment of the present invention.

*FIG. 7d is a perspective view of a folded zipper arrangement according to one embodiment.*

Figure 1:
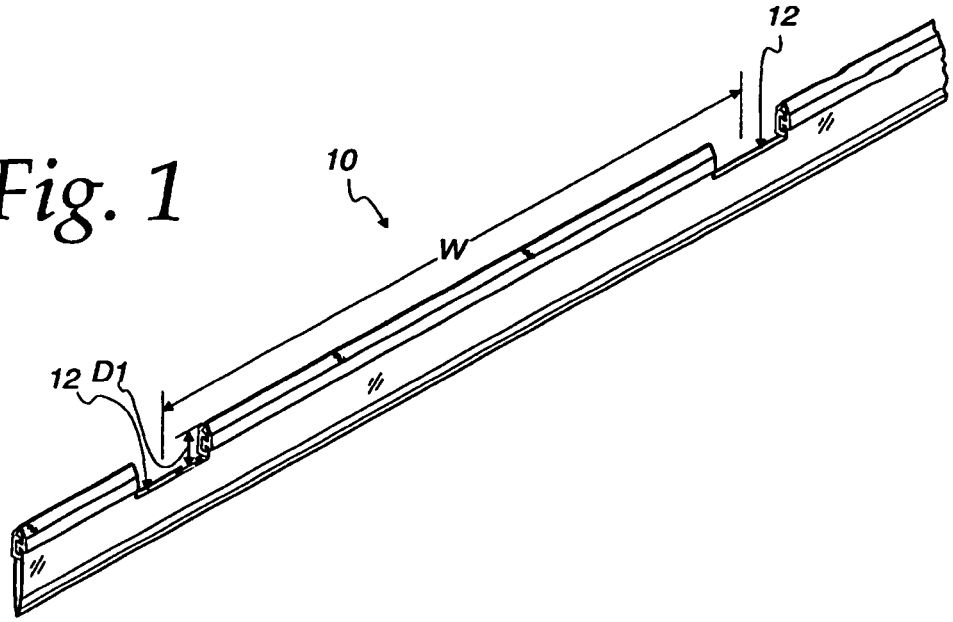
FIG. 1 is a perspective view of a zipper having spaced primary notches to be used in one embodiment of the present invention.

While the invention is susceptible to various modifications and alternative forms, specific embodiments thereof have been shown by way of example in the drawings and will herein be described in detail. It should be understood, however, that it is not intended to limit the invention to the particular forms disclosed but, on the contrary, to cover all modifications, equivalents, and alternatives falling within the spirit and scope of the invention as defined by the appended claims.

DESCRIPTION OF ILLUSTRATIVE EMBODIMENTS

Figure 2:
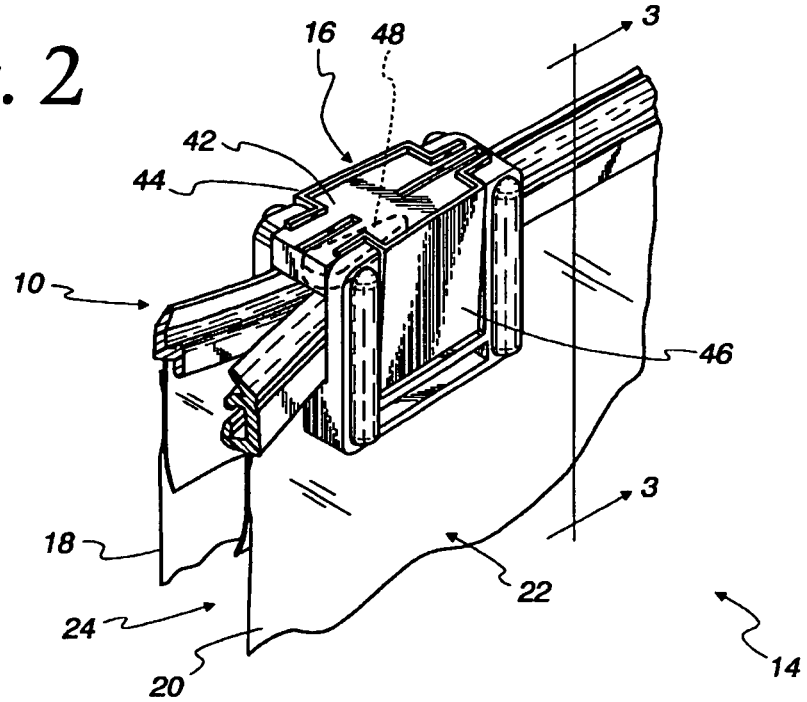
FIG. 2 is a perspective view of a portion of a recloseable package including a zipper and a slider according to one embodiment of the present invention.

Turning now to the drawings, FIG. 1 illustrates a zipper or fastener 10 having a plurality of generally aligned pairs of primary notches 12 according to one embodiment of the present invention. The primary notches 12 are shown as being spaced at a distance W that generally corresponds to a width of a thermoplastic bag. The primary notches 12 each have a distance D1 extending from a top surface of the zipper 10. FIG. 2 illustrates a mouth portion of a recloseable package or bag 14 having a slider 16 on the zipper 10, while FIG. 3 illustrates the zipper 10 of the mouth portion of the recloseable package 14 taken along line 3-3 of FIG. 2.

Referring to FIGS. 2 and 3, the mouth portion of the recloseable package 14 includes a pair of opposing wall panels 18 and 20 made of polymeric film, multi-layer and multi-component laminates, or co-extrusions. The pair of opposing wall panels 18 and 20 make up a package body 22 and define a receptacle space 24. Connected to the wall panel 18 is a male track 26 having a male profile 28 and a first fin portion 30 extending downward from the male profile 28. Connected to the other wall panel 20 is a female track 32 having a female profile 34 and a second fin portion 36 extending downward from the female profile 34.

The male and female profiles 28, 34 are releasably engageable with each other to provide a recloseable seal to the package. In the illustrated embodiment of FIG. 3, the lower edges of the first and second fin portions 30, 36 are joined to each other along a one time breakable preferential area of weakness or preferential tear area 38 to form a one time openable tamper evident feature 40. The fins may also be formed from one piece that has an area of weakness or preferential tear area. The joined first and second fin portions 30, 36 have a generally U-shaped or V-shaped cross-sectional configuration. The tamper evident feature 40 is described in detail in U.S. application Ser. No. 08/950,535, filed Oct. 15, 1997, and entitled "Reclosable Fastener Strip With Tamper Evident Feature," now U.S. Pat. No. 5,964,532 which is incorporated herein by reference in its entirety.

It is not necessary that the first and second fin 30, 36 be releasably engaged to each other by a one time breakable preferential area of weakness. For example, the first fin 30 may be separate from the second fin 36 according to another embodiment of the present invention.

The recloseable package 14 has the slider 16 (FIG. 2) slidably mounted to the zipper 10 for movement between a closed and open position. The male and female profiles 28, 34 are engaged to each other, while the slider 16 is in the closed position, and movement of the slider 16 from the closed position to the open position disengages the male and female profiles 28, 34 from each other. The manner of operation of this zipper and slider arrangement is described in detail in U.S. Pat. No. 5,063,644 to Herrington, Jr. et. al., which is incorporated herein by reference in its entirety.

The sliders to be used in the present invention may include various sliders that are adapted to move and disengage the male and female profiles 28, 34 from each other. One such slider (slider 16) is depicted in FIG. 2. The slider 16 of FIG. 2 is generally U-shaped and includes a transverse support member 42 with two depending legs 44, 46 therefrom. A separator finger 48 depends from the transverse support member 42 and is disposed between the depending legs 44, 46. The separator finger 48 extends at least partially between the male and female profiles 28, 34 to aid in disengaging the male and female profiles 28, 34 as the slider 16 is moved along the zipper 10.

FIG. 4 illustrates a zipper arrangement 50 comprising a zipper 52 and a plurality of the sliders 16. A slider 16a is located in a spaced primary notch 12, while the slider 16b is shown in a position straddling the male and female profiles. Referring to FIGS. 1, 3 and 4, the male track 26 has a plurality of spaced first primary notches 12a interrupting the male profile 28, while the female track 32 has a plurality of second primary notches 12b interrupting the female profile 34. The first primary notches 12a are generally aligned with the second primary notches 12b to form the aligned pairs of primary notches 12. The sliders 16 are adapted to slide onto the male and female profiles 28, 34 via the respective aligned pairs of primary notches 12. At least one of the first and second primary notches 12a, 12b may interrupt a portion of the first fin 30 and/or the second fin 36, respectively.

According to another embodiment of the present invention, the zipper may have one slider instead of the plurality of sliders described in the zipper arrangement of FIG. 4. According to another embodiment of the present invention, the zipper may have one first primary notch and/or one second primary notch. Likewise, the zipper may have one secondary notch.

The plurality of primary notches 12 are preferably located near the ends of the recloseable package 14 for a variety of reasons. For example, locating the primary notches 12 near the ends of the package 14 is generally more aesthetically pleasing to customers. In addition, this location allows the slider 16 to move and open the package 14 across a greater distance, resulting in a wider mouth of the package 14. Locating the primary notches 12 near the ends of the package 14 may also assist in forming the side seals of the package 14 since the profiles do not need to be flattened. Side seals of the package 14 may be formed more easily and/or efficiently because of the reduction or elimination in temperatures, pressures, and times associated with fusing the male and female profiles 28, 34 together near the ends of the package 14. Locating the primary notches near the ends of the package 14 may eliminate the need to fuse the male and females profiles 28, 34 together if the male and female profiles 28, 34 are cut away at the areas where the side sealing occurs.

The relationship between the notch 12 and the slider 16 will be discussed with respect to FIG. 4. A distance D1 of the notch preferably is less than a distance D3 (the internal opening of the slider 16) so that the slider may be placed more easily onto the profiles. As shown in FIG. 4, the sliders 16a, 16b overlap a portion of the fins to assist in aligning the position of the sliders 16a, 16b prior to threading onto the profiles. Specifically, the opening of the sliders 16a, 16b between the slider wings falls between the fins. The aligned primary notch 12 preferably has a width that is greater than a length L of the slider 16. The aligned primary notches 12 of FIGS. 1 and 4 are shown as extending through the respective male and female profiles in a direction generally transverse to a length of the zipper 16. The primary notches 12 do not, however, extend entirely through the first fin 30 and the second fin 36, respectively, in FIG. 4.

According to another embodiment of the present invention, the zipper may include a plurality of secondary notches. Referring specifically to FIG. 4, the male track 26 of the zipper arrangement 50 is further interrupted by a plurality of optional first secondary notches 54a, while the female track 32 is further interrupted by a plurality of optional second secondary notches 54b according to another embodiment of the invention. The first secondary notches 54a are generally aligned with the second secondary notches 54b to form generally aligned pairs of secondary notches 54. The aligned notches 54 have a distance D2 extending from a top surface of the zipper 52.

The secondary notches 54 are not adapted to engage the separator finger 48 of the zipper 16 which inhibits or prevents the slider 16 from disengaging the male and female profiles 28, 34. In other words, the separator 48 is ineffective to force a top portion (the ears) of the male and female profiles 28, 34 apart so as open the package 14. The slider is considered to be "parked" when it is in this condition. The secondary notches 54 also give a user of the package 14 the feel of a secure closure and assurance that the bag is closed with certainty. The secondary notches are described in detail in U.S. Pat. No. 5,067,208, which is incorporated herein by reference in its entirety.

The secondary notches 54 are preferably located at the closed end of the bag. As shown in FIG. 4, the first and second secondary notches 54a, 54b extend at least partially into the respective male and female profiles 28, 34. The aligned secondary notches 54 may be merged into respective aligned primary notches 12 as shown in FIG. 4.

Figure 5:
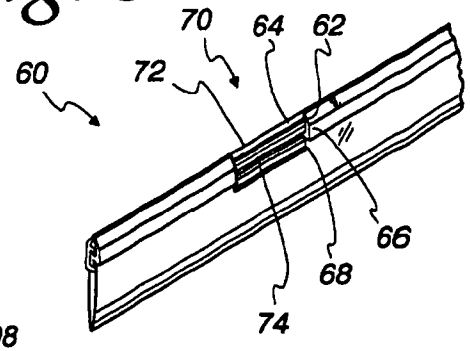
FIG. 5 is a perspective view of a zipper having spaced primary notches according to yet another embodiment of the present invention.

According to another embodiment (FIG. 5) to be used in the present invention, a zipper 60 comprises a male track 62 and a female track 64. The male track includes a male profile 66 and a first fin 68. The male track 62 has a plurality of spaced primary notches 70 interrupting the male profile 66. The female track is shown in FIG. 5 as being continuous, and includes a female profile 72 and a second fin 74. A slider (e.g., the slider in FIG. 4) is adapted to be placed onto the female profile 72 in an area where the primary notch 70 has been formed. The slider is slid onto the male profile 66 via the primary notch 70. The zipper 60 may include one slider or a plurality of sliders. Likewise, according to yet another embodiment, a slider may be placed onto a continuous male track (not shown) in an area where the female track has been interrupted by a primary notch. Then, the slider is slid onto the female profile via the primary notch.

According to yet another embodiment of the present invention, a zipper (not shown) comprises a male track and a female track. The male track includes a male profile and the female track includes a female profile. Neither the male track nor the female track comprises a first fin or a second fin, respectively, according to this embodiment. The zipper includes a plurality of generally aligned primary notches formed in the zipper. According to one embodiment of the present invention, a slider may be placed in a respective one of the plurality of aligned primary notches. A slider is then slid onto the male and female profiles via a respective one of the aligned primary notches. Alternatively, a plurality of sliders are slid onto the male and female profiles via respective ones of the aligned primary notches. Alternatively, a primary notch may interrupt only one of the profiles, as described above with respect to FIG. 5.

Figure 6:
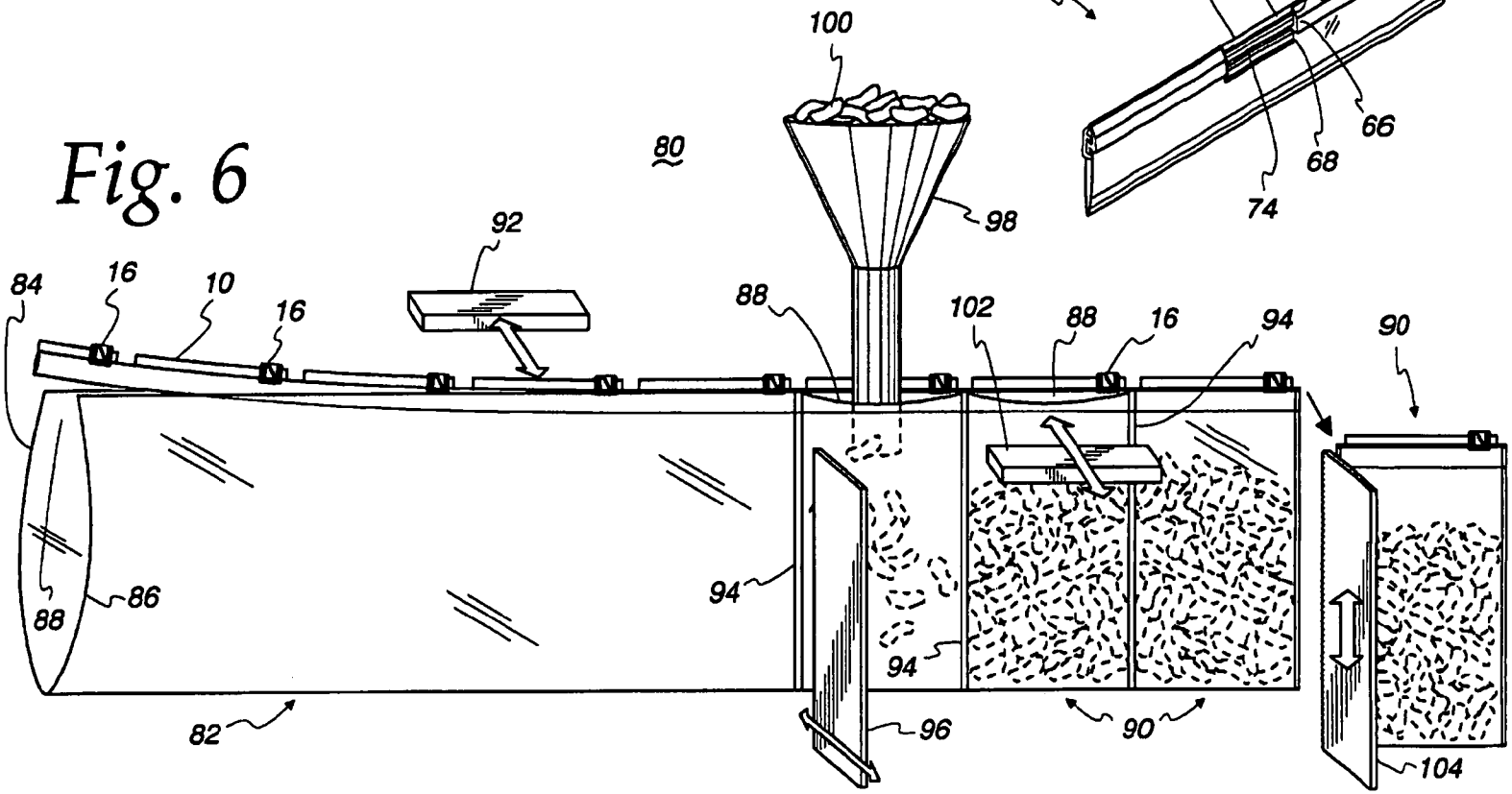
FIG. 6 is a diagram of basic components of a form, fill and seal machine.

A filled and sealed food or storage bag may be formed by a form, fill and seal machine. The zipper arrangement of FIG. 6 includes a zipper 10 and a plurality of sliders 16. Bag film or web 82, zippers 10, and sliders 16 are components for assembling into a complete bag. A schematic illustration of a form, fill and seal machine 80 is provided in FIG. 6. As depicted at the left side of FIG. 6, the plastic film or web 82 and a zipper 10 with sliders 16 thereon are fed into the form, fill and seal machine 80. The web 82 has already been formed into a generally U-shape to define a first side wall 84, a second side wall 86, and an open top 88 that will become finished individual bags 90. In FIG. 6, the sliders 16 are shown as mounted on the zipper 10, but the sliders 16 may be first assembled and accumulated, and then mounted on the zipper 10 by the form, fill and seal machine 80.

The zipper 10 with the sliders 16 of FIG. 6 is attached to the first side wall 84 of the web 82 by a heated seal bar 92. Side seals 94 are then formed in the web 82 by a second heated seal bar 96, leaving the open top 88 as the only access to the interior of the formed bag 90. Another second heated seal bar (hidden in FIG. 6) is typically located on the opposite side of the second heated seal bar 96 and works in conjunction with the seal bar 96 in forming the side seals 94. The bag 90 is then moved under a fill spout 98 through which a product 100 is deposited into the interior of each bag 90. As discussed above, product 100 may be nuts, candy, snacks, ingredients, salt, cheese, and other food and non-food products. After the bag 90 is filled, the second side wall 86 of the bag 90 is sealed to the zipper 10 by a third heated seal bar 102. The individual bags 90 are then separated from each other by a knife 104 that cuts the web 82 at the side seals 94. The filled bags 90 can then be shipped to retailers for sale to consumers.

The bag 90 may have an end termination or stop (not shown) for inhibiting or preventing the slider 16 from going past the ends of the zipper. The end terminations also hold the male and female profiles together to resist stresses applied to the profiles during normal use of the plastic bag. One type of end termination is in the form of a strap/clip that wraps over the top of a zipper. Further information concerning such an end termination may be found in U.S. Pat. No. 5,067,208, which is incorporated herein by reference in its entirety. One end of the strap is provided with a rivet-like member that penetrates through the zipper fins and into a cooperating opening at the other end of the strap. Other types of end termination are disclosed in U.S. Pat. Nos. 5,482,375, 5,448,807, 5,442,837, 5,405,478, 5,161,286, 5,131,121 and 5,088,971, which are each incorporated herein by reference in their entireties.

The bag 90 may also have an end termination formed from first and second upstanding panels (not shown) extending upwardly from the respective first and second body panels. The opposing ends of the first upstanding panels are connected to the respective opposing ends of the second upstanding panel to form an open pocket in which the slider and zipper are captured. This is discussed in further detail in U.S. Pat. No. 5,713,669, which is incorporated herein by reference in its entirety.

The form, fill and seal machines may produce the bags in a different manner than as described in FIG. 6. For example, the individual bags 90 may be separated from each other by the knife 104 after side seals 94 are formed in the bags by the seal bar 96, but before the individual bags 90 are filled with product 100 and sealed with top seal 102. The zipper 10 with sliders 16 may be located at the bottom or c-fold of the web 82, opposite the open top 88. Other variations of the described form, fill and seal process of FIG. 6 are contemplated, such as, for example, having the zipper 10 sealed on the bag 90 after it has been filled with product 100. It is contemplated that the zipper and zipper arrangements of the present invention may be used in other bag making/packaging processes.

Prior to being used in, for example, a form, fill and seal machine, a zipper may be stored by a variety of methods, including being folded in a box. One example of a folded zipper arrangement 120 is shown in FIGS. 7b and 7c. The folded zipper arrangement 120 may, for example, have a similar shape as shown in FIG. 1. The folded zipper arrangement 120 includes first and second opposing tracks where the first track has a plurality of first primary notches interrupting the male profile and the second track has a plurality of spaced second primary notches interrupting the second profile. The second primary notches are generally aligned with respective ones of the first primary notches to form aligned pairs of primary notches 124.

Figure 7A:
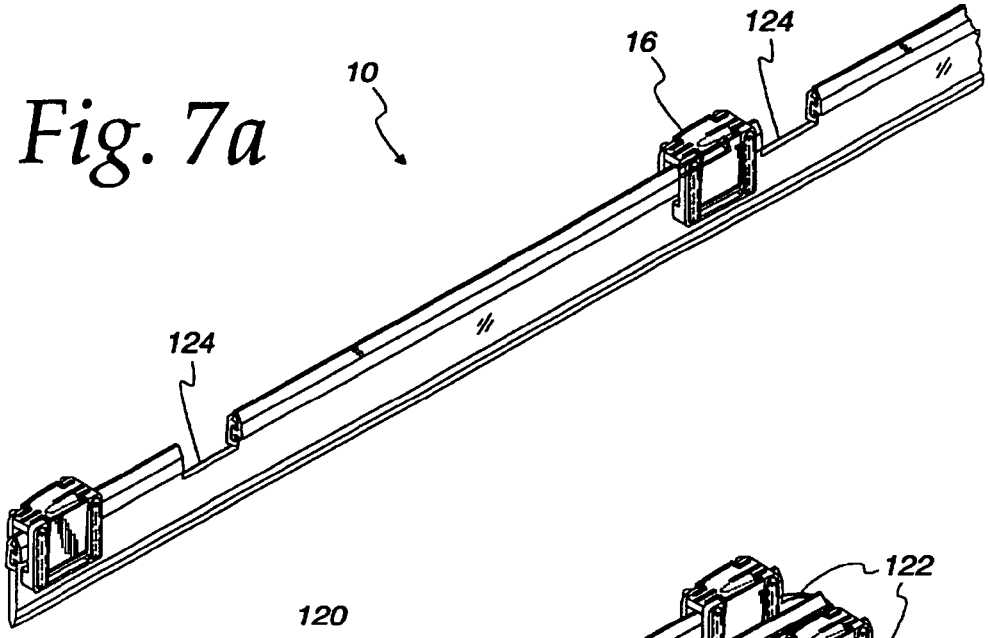
FIG. 7a is a perspective view of a zipper arrangement to be folded according to a further embodiment of the present invention.
Figure 7B:
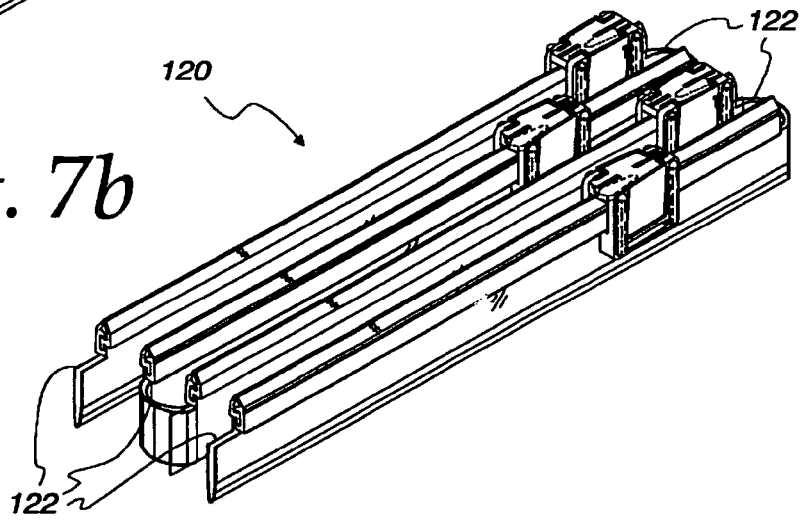
FIG. 7b is a perspective view of a folded zipper arrangement according to another embodiment of the present invention.
Figure 7C:
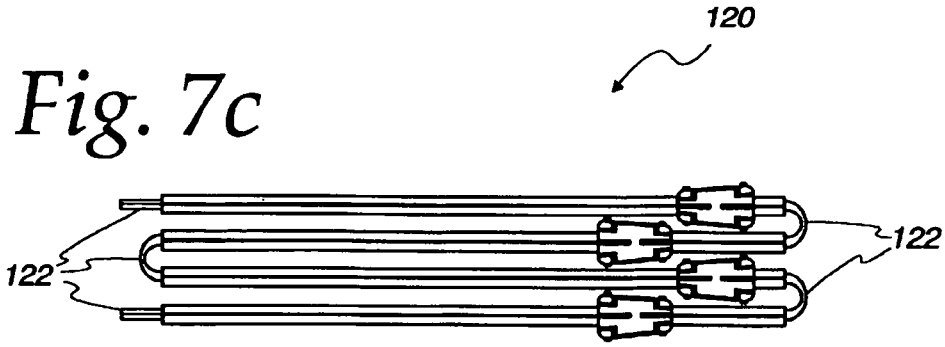
FIG. 7c is a top view of the folded zipper arrangement of FIG. 7b.

Referring to FIGS. 7a-c, the zipper 120 also includes a plurality of fold regions or areas 122 to assist in folding the zipper 120. The plurality of fold areas 122 are generally transverse to a length of the zipper 10 and are aligned with respective ones of the aligned pairs of primary notches 124. The fold areas 122 divide the zipper 120 into a plurality of zipper segments. The zipper segments of the folded zipper 120 are generally parallel to each other and generally correspond to a width of a thermoplastic bag. The zipper 120 may also include fold lines that assist in folding the zipper 120, such as, for example, score lines. The zipper may also include a breakable line of weakness or an area of weakness [(not shown)] *121* (*see FIG. 7d*) located in the fold areas to assist in separating portions of the zipper from the remainder thereof. These perforation lines may be used in a method where the bag has been filled with product and the zipper is later added to the filled bag. The zipper 120 of FIGS. 7a-c is shown as being folded in a general shape of an accordion or z-fold along the fold areas 122.

Figure 5A:
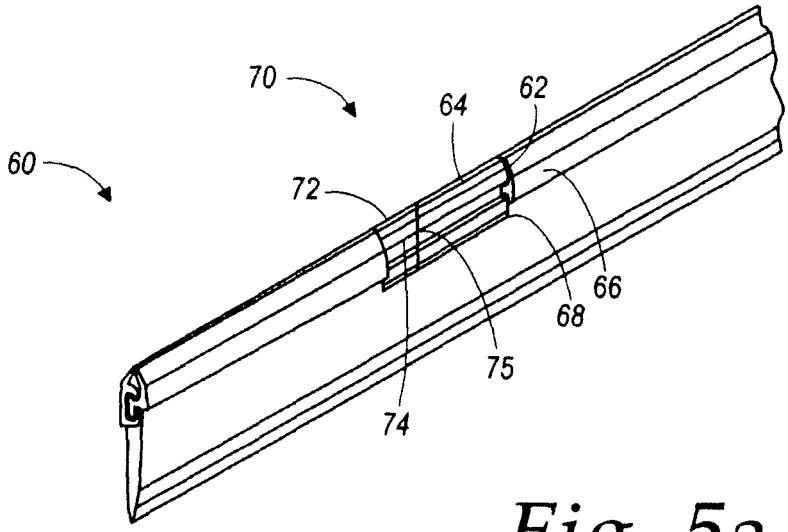
*FIG. 5a is a perspective view of a zipper having spaced primary notches according to one embodiment.*

In another embodiment, a zipper includes a plurality of fold areas or regions to assist in folding the zipper along the fold areas. The zipper has a first track with a plurality of spaced primary notches interrupting the first profile and a second track with a plurality of spaced slits [(not shown)] *75* (*see FIG. 5a*) interrupting the second profile. The slits are generally aligned with respective ones of the primary notches. The plurality of fold areas are generally aligned with respective ones of the aligned slits and primary notches. The zipper may include a breakable line of weakness or an area of weakness (not shown) located in the fold areas to assist in separating portions of the zipper from the remainder thereof.

It is contemplated, however, that the zipper may be folded in other shapes, such as being rolled or packed. The zipper 120 of one box may be spliced to a zipper arrangement (not shown) of a second box. The zipper may also be folded without the sliders 16 (not shown).

The zipper arrangement and sliders of the present invention may be made from a variety of suitable materials. Some examples of materials that may be used in forming the profiles, tracks, and fins include the following resins: high density polyethylene (HDPE), linear low density polyethylene (LLDPE), metallocenecatalyzed LLDPE, polypropylene (PP), ethylene-propylene copolymer (E-P copolymer), ethylene vinyl acetate copolymer (EVA), low density polyethylene (LDPE), very low density polyethylene (VLDPE), and nylon.

The fins may be comprised of a plurality of layers where the outer layer is made of a lower melting temperature material and the inner layer is made of a higher melting temperature material to assist in inhibiting fusion of the fins. Similarly, one fin may be made of a plurality of layers where the outer layer is made of a lower melting temperature material and the inner layer is made of a higher melting temperature material. For example, the lower melting temperature materials may include EVA, LDPE, VLDPE, LLDPE, and metallocene-catalyzed LLDPE.

The slider may be molded from any suitable plastic, such as, for example, nylon, polypropylene, polystyrene, Delrin, or ABS. The opposing wall panels may be made from any suitable thermoplastic film such as, for example, polyethylene, polypropylene, polyester, copolyester, or mixtures thereof. Furthermore, the wall panels of the present invention can have multiple layers joined by coextrusion or lamination. Thus, one skilled in the art can design and coextrude multilayered polymeric bags which will incorporate the various properties inherent in differing polyethylene and polypropylene compositions. It is further possible to incorporate pigments, metallic components, paper, and/or paper/plastic composites into or on the layer or layers of the polymeric bags of the instant invention.

Methods of Forming Notches

Figure 8:
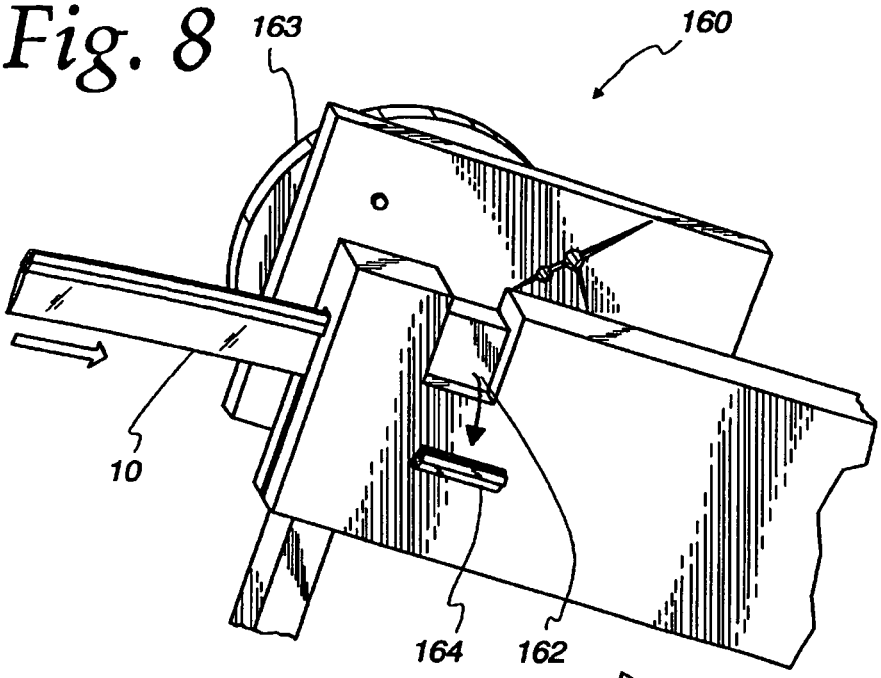
FIG. 8 is a perspective view of a punching apparatus for forming spaced primary notches in a zipper according to one embodiment of the present invention.

The primary notches and optional secondary notches may be formed by a variety of methods. For example, one method of forming the primary notches in a zipper is shown in FIG. 8. FIG. 8 illustrates a punching apparatus 160 that forms aligned primary notches. The punching apparatus 160 includes a movable member 162 and an air cylinder mechanism 163. The air cylinder mechanism 163 controls the movement of the moveable member 162.

The moveable member 162 is shown in FIG. 8 as punching aligned primary notches that extend through the male and female profiles. The moveable member 162 preferably leaves at least a portion of the first and second fins so as to allow a slider to be placed onto a cut edge of the fins. A portion 164 from the zipper 10 is shown as being discharged from the zipper 10 by the moveable member 162. The moveable member 162 notches the zipper 10 at desired intervals, such as intervals being about a bag distance apart.

The punching apparatus 160 may also contain a second moveable member (not shown) that can form a plurality of secondary notches in a similar manner as described above for the moveable member 162. Alternatively, the punching apparatus may comprise a tiered moveable member (not shown) that simultaneously punches a plurality of aligned primary and secondary notches. According to another embodiment, a punching apparatus (not shown) may be designed to punch a first track without punching a second track. One such punching apparatus would include a moveable member located vertically above the zipper and adapted to move in a downward direction for punching a first track without punching a second track. This embodiment may be employed without first separating the male and female profiles.

Method of Placing at Least One Slider onto a Zipper

Figure 9:
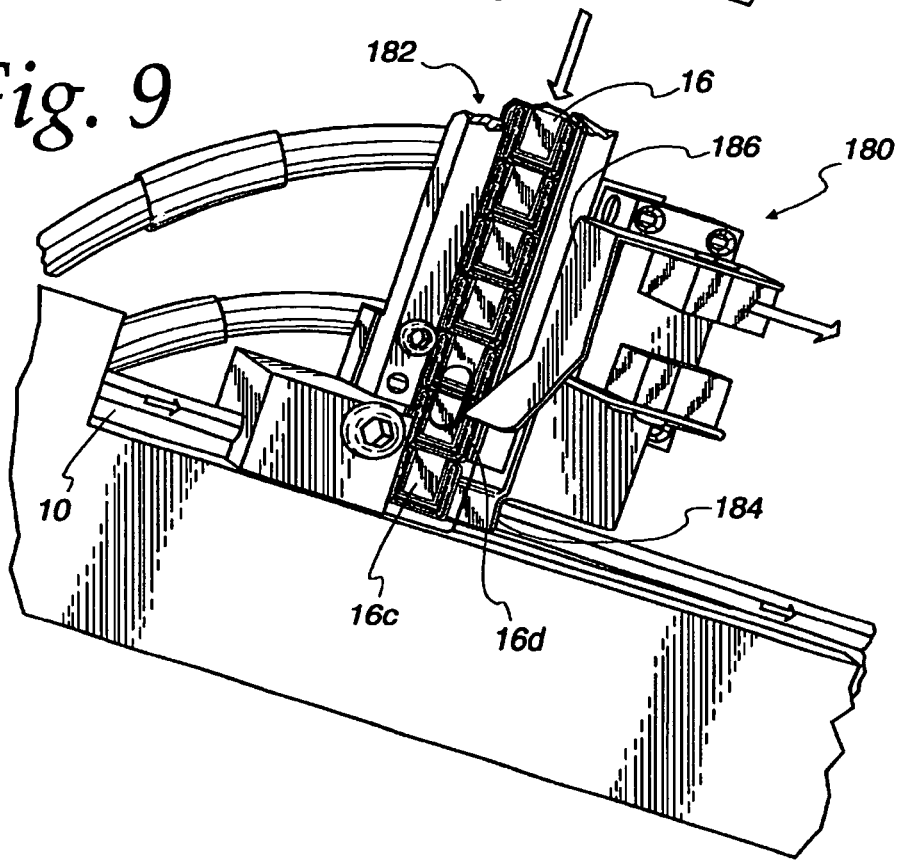
FIGS. 9-11 epict an operational sequence using an escapement mechanism for placing sliders onto a zipper according to one method of the present invention.
Figure 10:
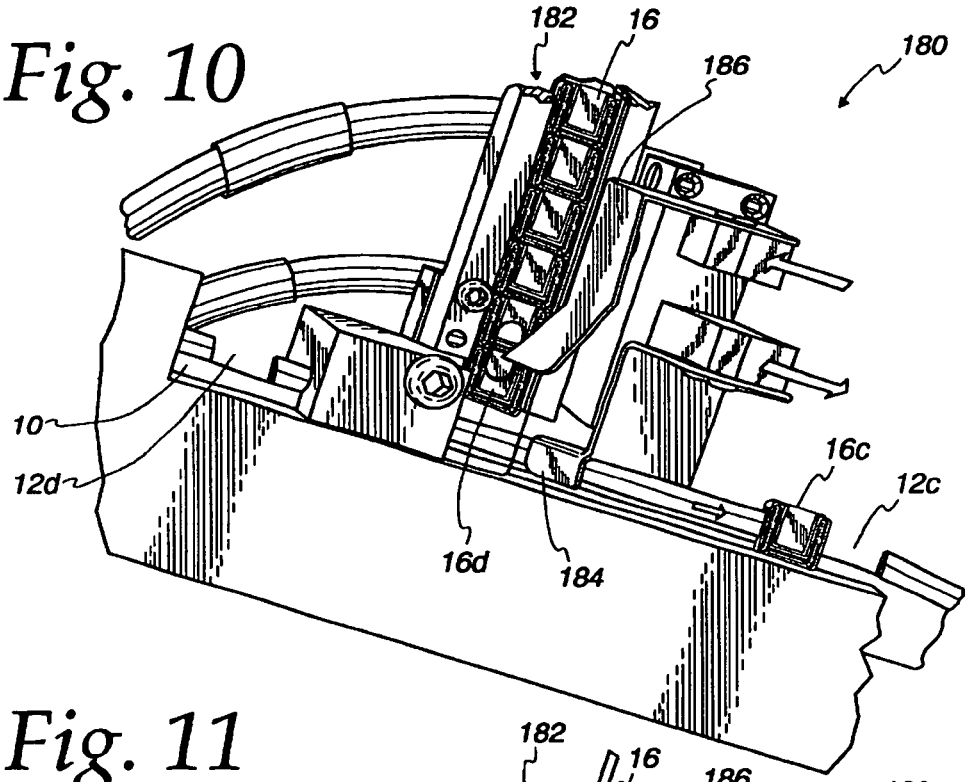
Figure 11:
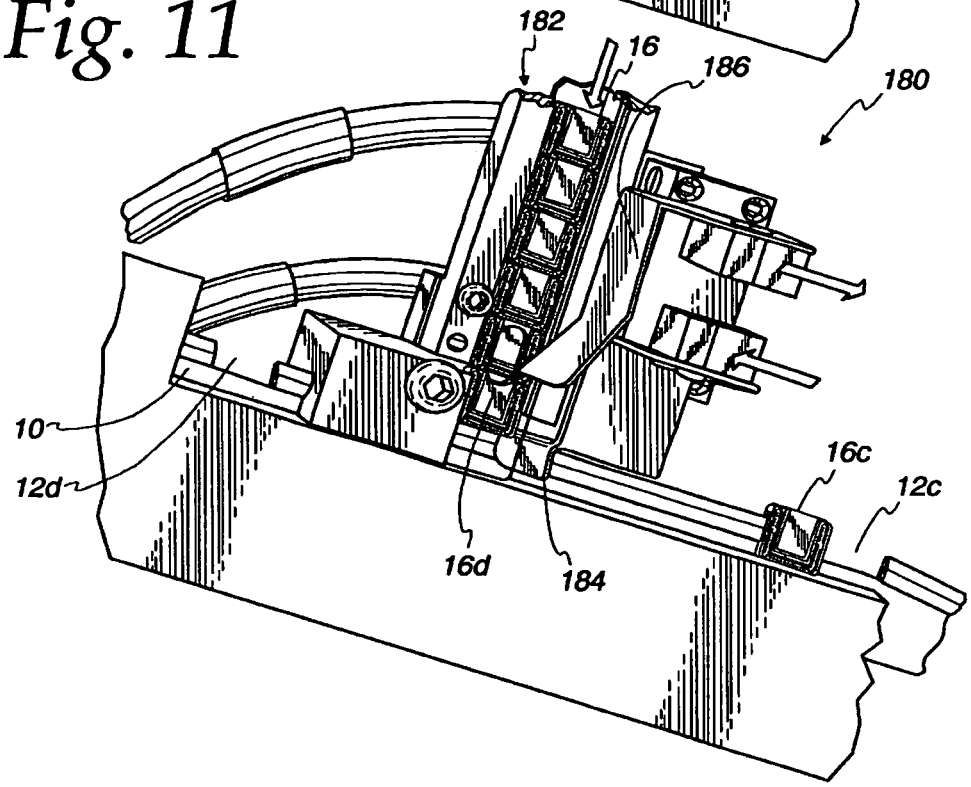

One method of placing at least one slider onto a zipper is shown in FIGS. 9-11. Referring to FIG. 9, an escapement mechanism 180 drops the sliders 16 one at a time in respective ones of the aligned pairs of the primary notches of the zipper 10. The escapement mechanism 180 is located downstream from the punching apparatus 160 of FIG. 8. The escapement mechanism 180 is preferably one bag repeat downstream from the punching apparatus 160. The escapement mechanism 180 may be located upstream from the form, fill and seal machine discussed above in FIG. 6.

The escapement mechanism 180 comprises a slider holder 182, a threader or slider finger 184, and a restraining finger 186. The slider holder 182 is designed to be compatible with an assembly of sliders 16 or individual sliders. The slider holder 182 includes a vertical column with a channel sized to hold the sliders 16. The channel of the slider holder 182 includes an open top and an open bottom. It is contemplated that the slider holder 182 may be shaped in a different manner than shown in FIG. 9. For example, the slider holder may be rectangular or square. Additional examples are shown in the application entitled "Assembly And Accumulation Of Sliders For Profiled Zippers", Ser. No. 09/307,893 which has been filed concurrently with this application, and is incorporated herein be reference in its entirety. The shape of the slider holder generally corresponds to the shape of the assembly of the sliders or individual sliders. The slider holder 182 is preferably designed to allow one slider 16 at a time to be placed in a primary notch of the zipper 10.

As shown in FIG. 9, a zipper 10 is advanced toward the escapement mechanism 180 in a direction of the arrow. The zipper 10 may be pushed or pulled through the escapement mechanism 180. At a time when one of the aligned pairs of primary notches is generally located below the open bottom of the channel of the slider holder 182, a slider 16c is dropped in the aligned pair of primary notches (hidden in FIG. 9) of the zipper 10. The slider 16c may be placed in the notches by gravity and driven mechanically or electro-mechanically. The zipper 10 continues to move forward through the escapement mechanism 180. The threader finger 184 engages the dropped slider 16c and holds it in place as the zipper 10 is either pushed or pulled such that the slider 16c is threaded onto the profiles. An edge of the slider 16c abuts the threader finger 184 and is prevented from moving forward with the zipper 10. Thus, the aligned pair of primary notches is moving away from the slider 16c, while the slider 16c is being moved along the male and female profiles.

Referring to FIG. 10, the threader finger 184 is then moved away from the path of the slider 16c, resulting in the slider 16c moving forward with the zipper 10. The movement of the threader finger 184 from the path of the slider 16c corresponds to the desired placement of the slider 16c relative to a primary notch 12c. If a greater distance is desired between the slider 16c and the notch 12c, then the threader finger 184 remains abutting the slider 16c for a longer period of time. At the same time that the threader finger 184 is moved from the path of the slider 16c, the restraining finger 186 is moved toward the sliders 16. The restraining finger 186 holds the next slider (16d) in place as the zipper 10 is being advanced through the escapement mechanism 180.

According to this embodiment, the threader finger 184 and the restraining finger 186 are powered by independent pistons. Internal air passages allow only one of the threader finger 184 and the restraining finger 186 to be fully retracted when the other is completely extended. Referring to FIG. 11, the threader finger 184 is returned to the same position shown in FIG. 9 after the slider 16c has advanced past the threader finger 184. At the same time, the restraining finger 186 returns to a position away from the assembly of sliders 16. The next slider (16d) will be placed into an aligned pair of primary notches 12d as the zipper 10 is advanced forward.

According to one embodiment, the slider to be used in the method described above may be of the type described above in FIG. 2. A separator finger of the slider may extend at least partially between the male and female profiles so as to disengage the male and female profiles in response to movement along the zipper. It is preferable that the slider be positioned in the primary notch so that the separator finger of the slider remains between the male and female profiles.

According to another method of the present invention, a slider may be placed on a zipper as described above. The zipper may be of a length generally corresponding to a width of the bag after the slider is placed on the zipper.

According to yet another method of the present invention, a slider may be placed onto a zipper where only a first track has a plurality of spaced primary notches interrupting a first profile. In this method, the sliders are pushed downward onto a second profile and into respective ones of the primary notches. The sliders are slid onto the first profile via the respective primary notches. This method may use a similar type of escapement mechanism 180 that would allow the sliders to be pushed downward onto a second profile. The sliders of the type described above in FIG. 2 are preferably positioned so that a separator finger of the slider remains between the male and female profiles. Additional, a slider may be placed on a zipper having a length generally corresponding to a width of the bag after the slider is placed on the zipper.

While the present invention has been described with reference to the particular embodiments illustrated, those skilled in the art will recognize that many changes and variations may be made thereto without departing from the spirit and scope of the present invention. The embodiments and obvious variations thereof are contemplated as falling within the scope and spirit of the claimed invention, which is set forth in the following claims.

What is claimed is:

1. A zipper arrangement for use in manufacturing thermoplastic bags, said zipper arrangement comprising:

a zipper including first and second opposing tracks, said first track having a first profile and said second track having a second profile, said first and second profiles being releasable engageable to each other, said first track having one or more spaced primary notches interrupting said first profile; wherein said first track has a first fin extending downward from said first profile, wherein said first fin is detachably connected to said second fin, and at least one slider inserted onto said first profile via one of said primary notches, said slider being adapted to engage and disengage said first and second profiles in response to movement along said zipper.

2. A zipper arrangement for use in manufacturing thermoplastic bags, said zipper arrangement comprising:

a zipper including first and second opposing tracks, said first track having a first profile and said second track having a second profile, said first and second profiles being releasably engageable to each other, said first track having one or more spaced primary notches interrupting said first profile; and at least one slider inserted onto said first profile via one of said primary notches, said slider being adapted to engage and disengage said first and second profiles in response to movement along said zipper, wherein a depth of said primary notches is less than an internal opening of said slider.

3. A zipper arrangement for use in manufacturing thermoplastic bags, said zipper arrangement comprising:

a zipper including first and second opposing tracks, said first track having a first profile and said second track having a second profile, said first and second profiles being releasable engageable to each other, said first track having one or more spaced primary notches interrupting said first profile;

at least one slider inserted onto said first profile via one of said primary notches, said slider being adapted to engage and disengage said first and second profiles in response to movement along said zipper, wherein said slider is pushed downward onto said second profile.

4. A zipper arrangement for use in manufacturing thermoplastic bags, said zipper arrangement comprising:

a zipper including first and second opposing tracks, said first track having a first profile and one or more spaced first primary notches interrupting said first profile, said second track having a second profile and one or more spaced second primary notches interrupting said second profile, said second primary notches being generally aligned with respective ones of said first primary notches to form one or more aligned pairs of primary notches, said first and second profiles being releasably engageable to each other; wherein said first track has a first fin extending downward from said first profile, wherein said second track has a second fin extending downward from said second profile, wherein said first fin is detachably connected to said second fin, and at least one slider inserted onto said zipper via one of said aligned pairs of primary notches, said slider being adapted to engage and disengage said first and second profiles in response to movement along said zipper.

5. A zipper arrangement for use in manufacturing thermoplastic bags, said zipper arrangement comprising:

a zipper including first and second opposing tracks, said first track having a first profile and one or more spaced first primary notches interrupting said first profile, said second track having a second profile and one or more spaced second primary notches interrupting said second profile, said second primary notches being generally aligned with respective ones of said first primary notches to form one or more aligned pairs of primary notches, said first and second profiles being releasably engageable to each other; and at least one slider inserted onto said zipper via one of said aligned pairs of primary notches, said slider being adapted to engage and disengage said first and second profiles in response to movement along said zipper, wherein a depth of said first primary notches is less than an internal opening of said sliders.

6. A zipper arrangement for use in manufacturing thermoplastic bags, said zipper arrangement comprising:

a zipper including first and second opposing tracks, said first track having a first profile and one or more spaced first primary notches interrupting said first profile, said second track having a second profile and one or more spaced second primary notches interrupting said second profile, said second primary notches being generally aligned with respective ones of said first primary notches to form one or more aligned pairs of primary notches, said first and second profiles being releasably engageable to each other; wherein a depth of said first primary notches is less than an internal opening of said sliders; and at least one slider inserted onto said zipper via one of said aligned pairs of primary notches, said slider being adapted to engage and disengage said first and second profiles in response to movement along said zipper, wherein a depth of said second primary notches is less than an internal opening of said sliders.

7. A zipper arrangement for use in manufacturing thermoplastic bags, said zipper arrangement comprising:

a zipper including first and second opposing tracks, said first track having a first profile and one or more spaced first primary notches interrupting said first profile, said second track having a second profile and one or more spaced second primary notches interrupting said second profile, said second primary notches being generally aligned with respective ones of said first primary notches to form one or more aligned pairs of primary notches, said first and second profiles being releasably engageable to each other; wherein said first track includes one or more first secondary notches and said second track includes one or more second secondary notches, said second secondary notches being generally aligned with respective ones of said first secondary notches to form aligned pairs of secondary notches, said first and second secondary notches extending at least partially into said respective first and second profiles, and at least one slider inserted onto said zipper via one of said aligned pairs of primary notches, said slider being adapted to engage and disengage said first and second profiles in response to movement along said zipped.

8. The zipper arrangement of claim 7, wherein said slider includes a respective separator finger that extends at least partially between said first and second profiles to aid in disengaging said first and second profiles as said slider is moved along said zipper, at least one of said aligned pairs of secondary notches being adapted to engage said separator finger of one of said respective slider.

9. A zipper arrangement for use in manufacturing thermoplastic bags, said zipper arrangement comprising:

a zipper including first and second opposing tracks, said first track having a first profile and one or more spaced first primary notches interrupting said first profile, said second track having a second profile and one or more spaced second primary notches interrupting said second profile, said second primary notches being generally aligned with respective ones of said first primary notches to form one or more aligned pairs of primary notches, said first and second profiles being releasable engageable to each other; wherein said first track includes one or more first secondary notches and said second track includes one or more second secondary notches, said second secondary notches being generally aligned with respective ones of said first secondary notches to form aligned pairs of secondary notches, said first and second secondary notches extending at least partially into said respective first and second profiles; wherein said first primary notches merge into respective ones of said first and secondary notches, and at least one slider inserted onto said zipper via one of said aligned pairs of primary notches, said slider being adapted to engage and disengage said first and second profiles in response to movement along said zipper, at least one of said aligned pairs of secondary notches being adapted to park a respective one of said sliders.

10. A folded zipper for use in manufacturing thermoplastic bags, said zipper comprising:

first and second opposing tracks, said first track having a first profile and one or more spaced first primary notches interrupting said first profile, said second track having a second profile and one or more spaced second primary notches interrupting said second profile, said second primary notches being generally aligned with respective ones of said first primary notches to form aligned pairs of primary notches said first and second profiles being releasably engageable to each other;

said zipper including a plurality of fold areas generally transverse to a length of said zipper and aligned with respective ones of said aligned pairs of notches, said zipper being folded along said fold areas.

11. The folded zipper of claim 10, wherein said zipper is folded in a general shape of an accordion.

12. The folded zipper of claim 10, wherein said fold areas divide said zipper into a plurality of zipper segments, said zipper segments of said folded zipper being generally parallel to each other.

13. The folded zipper of claim 10, wherein said first track has a first fin extending downward from said first profile and said second track has a second fin extending downward from said second profile.

14. The folded zipper of claim 13, wherein said first fin is detachably connected to said second fin.

15. The folded zipper of claim 10, further including at least one slider inserted onto said zipper via a respective one of said aligned pairs of primary notches before said zipper is folded along said fold areas so as to form a folded zipper arrangement said slider being adapted to engage and disengage said first and second profiles in response to movement along said zipper.

16. The folded zipper of claim 15, wherein said at least one slider is a plurality of sliders.

17. The folded zipper of claim 10, wherein said fold areas include respective fold lines to assist in folding said zipper.

18. The folded zipper of claim 10, wherein said zipper further includes a breakable line of weakness or an area of weakness in said fold areas to assist in detaching portions of said zipper.

19. The folded zipper of claim 10, wherein said one or more first spaced primary notches is a plurality of first spaced primary notches and said one or more second spaced primary notches is a plurality of second spaced primary notches.

20. A method of making a folded zipper for use in manufacturing thermoplastic bags, said method comprising:

providing a zipper comprising a zipper, said zipper including first and second opposing tracks, said first track having a first profile and one or more spaced first primary notches interrupting said first profile, said second track having a second profile and one or more spaced second primary notches interrupting said second profile, said second primary notches being generally aligned with respective ones of said first primary notches to form aligned pairs of primary notches, said first and second profiles being releasably engageable to each other, said zipper including a plurality of fold areas generally transverse to a length of said zipper and aligned with respective ones of said aligned pairs of notches; and folding said zipper along said fold areas.

21. The method of claim 20, wherein said step of folding said zipper includes folding said zipper in a general shape of an accordion.

22. The method of claim 20, wherein said fold areas divide said zipper into a plurality of zipper segments, and wherein said step of folding said zipper is performed in a manner such that said zipper segments are generally parallel to each other.

23. The method of claim 20, wherein said first track has a first fin extending downward from said first profile and said second track has a second fin extending downward from said second profile.

24. The method of claim 23, wherein said first fin is detachably connected to said second fin.

25. The method of claim 20, wherein said zipper further includes at least one slider inserted onto said zipper via a respective one of said aligned pairs of primary notches before said zipper is folded along said fold areas so as to form a folded zipper arrangement, said slider being adapted to engage and disengage said first and second profiles in response to movement along said zipper.

26. The method of claim 25, wherein said at least one slider is a plurality of sliders.

27. The method of claim 20, wherein said fold areas include respective fold lines to assist in folding said zipper.

28. The method of claim 20, wherein said zipper further includes a breakable line of weakness or an area of weakness in said fold areas to assist in detaching portions of said zipper.

29. The method of claim 20, wherein said one or more first spaced primary notches is a plurality of first spaced primary notches and said one or more second spaced primary notches is a plurality of second spaced primary notches.

30. A method of placing a slider onto a zipper, said method comprising:

providing said zipper, said zipper including first and second opposing tracks, said first track having a first profile and said second track having a second profile, said first and second profiles being releasably engageable to each other, said first track having one or more spaced primary notches interrupting said first profile;

providing at least one slider, said slider being adapted to engage and disengage said first and second profiles in response to movement along said zipper;

mounting said slider onto said second profile and into a respective one of said primary notches; and sliding said slider onto said first profile via a respective one of said primary notches.

31. The method of claim 30, wherein said at least one slider is a plurality of sliders.

32. The method of claim 30, wherein said first track has a first fin extending downward from said first profile.

33. The method of claim 32, wherein said second track has a second fin extending downward from said second profile.

34. The method of claim 30, wherein said slider comprises a first side wall, a second side wall and transverse body member bridging said first and second side walls, said transverse body member including a separator finger.

35. The method of claim 30, wherein said slider comprises a separator finger, said separator finger extending at least partially between said first and second profiles so as to disengage said first and second profiles in response to movement along said zipper.

36. The method of claim 30, further including a step of positioning said slider so that a separator finger of said slider remains between said first profile and said second profile.

37. The method of claim 30, wherein said one or more first spaced primary notches is a plurality of first spaced primary notches.

38. A method of placing a slider onto a zipper, said method comprising:

providing said zipper, said zipper including first and second opposing tracks, said first track having a first profile and said second track having a second profile, said first and second profiles being releasably engageable to each other, said first track having one or more spaced primary notches interrupting said first profile; wherein said first track has a first fin extending downward from said first profile, wherein said second track has a second fin extending downward from said second profiles, wherein said first fin is detachably connected to said second fin, providing at least one slider, said slider being adapted to engage and disengage said first and second profiles in response to movement along said zipper;

mounting said slider onto said second profile and into a respective one of said primary notches; and sliding said slider onto said first profile via a respective one of said primary notches.

39. A method of placing a slider onto a zipper, said method comprising:

providing said zipper, said zipper including first and second opposing tracks, said first track having a first profile and one or more spaced first primary notches interrupting said first profile, wherein said first track has a first fin extending downward from said first profile, wherein said second track has a second fin extending downward from said second profile, wherein said first fin is detachably connected to said second fin, said second track having a second profile and one or more plurality of spaced second primary notches interrupting said second profile, said second primary notches being generally aligned with respective ones of said first primary notches to form generally aligned pairs of primary notches, said first and second profiles being releasably engageable to each other;

providing at least one slider, said slider being adapted to engage and disengage said first and second profiles in response to movement along said zipper;

positioning said slider in a respective one of said aligned pairs of primary notches; and sliding said slider onto said first and second profiles via a respective one of said aligned pairs of primary notches.

40. A folded zipper for use in manufacturing thermoplastic bags, said zipper comprising:

first and second opposing tracks, said first track having a first profile and one or more spaced primary notches interrupting said first profile, said second track having a second profile and one or more spaced slits interrupting said second profile, said slits being generally aligned with respective ones of said primary notches, said first and second profiles being releasably engageable to each other;

said zipper including a plurality of fold areas generally transverse to a length of said zipper and generally aligned with respective ones of said aligned slits and primary notches, said zipper being folded along said fold areas.

41. The folded zipper of claim 40, wherein said zipper is folded in a general shape of an accordion.

42. The folded zipper of claim 40, wherein said fold areas divide said zipper into a plurality of zipper segments, said zipper segments of said folded zipper being generally parallel to each other.

43. The folded zipper of claim 40, wherein said first track has a first fin extending downward from said first profile and said second track has a second fin extending downward from said second profile.

44. The folded zipper of claim 43, wherein said first fin is detachably connected to said second fin.

45. The folded zipper of claim 40, further including at least one slider inserted onto said zipper via a respective one of said primary notches before said zipper is folded along said fold areas so as to form a folded zipper arrangement, said slider being adapted to engage and disengage said first and second profiles in response to movement along said zipper.

46. The folded zipper of claim 45, wherein said at least one slider is a plurality of sliders.

47. The folded zipper of claim 40, wherein said fold areas include respective fold lines to assist in folding said zipper.

48. The folded zipper of claim 40, wherein said zipper further includes a breakable line of weakness or an area of weakness in said fold areas to assist in detaching portions of said zipper.

49. The folded zipper of claim 40, wherein said one or more first spaced primary notches is a plurality of first spaced primary notches.

50. The folded zipper of claim 40, wherein said one or more spaced slits is a plurality of spaced slits.

51. A method of making a folded zipper for use in manufacturing thermoplastic bags, said method comprising:

providing a zipper comprising a zipper, said zipper including first and second opposing tracks, said first track having a first profile and one or more spaced primary notches interrupting said first profile, said second track having a second profile and one or more spaced slits interrupting said second profile, said slits being generally aligned with respective ones of said primary notches, said first and second profiles being releasably engageable to each other, said zipper including a plurality of fold areas generally transverse to a length of said zipper and generally aligned with respective ones of said aligned slits and primary notches; and folding said zipper along said fold areas.

52. The method of claim 51, wherein said step of folding said zipper includes folding said zipper in a general shape of an accordion.

53. The method of claim 51, wherein said fold areas divide said zipper into a plurality of zipper segments, and wherein said step of folding said zipper is performed in a manner such that said zipper segments are generally parallel to each other.

54. The method of claim 51, wherein said first track has a first fin extending downward from said first profile and said second track has a second fin extending downward from said second profile.

55. The method of claim 54, wherein said first fin is detachably connected to said second fin.

56. The method of claim 51, wherein said zipper further includes at least one slider inserted onto said zipper via a respective one of said primary notches before said zipper is folded along said fold areas so as to form a folded zipper arrangement, said slider being adapted to engage and disengage said first and second profiles in response to movement along said zipper.

57. The method of claim 56, wherein said at least one slider is a plurality of sliders.

58. The method of claim 51, wherein said fold areas include respective fold lines to assist in folding said zipper.

59. The method of claim 51, wherein said zipper further includes a breakable line of weakness or an area of weakness in said fold areas to assist in detaching portions of said zipper.

60. The method of claim 51, wherein said one or more first spaced primary notches is a plurality of first spaced primary notches.

61. The method of claim 51, wherein said one or more spaced slits is a plurality of spaced slits.

62. A method of forming and filling a package, said method comprising:

providing a zipper having one or more spaced primary notches interrupting a portion of said zipper;

mounting a slider onto said zipper via a respective one of said primary notches, said slider being adapted to open and close said zipper;

attaching said zipper to a web of thermoplastic film;

forming said zipper-carrying web of film into a package having an open end;

filling said package via said open end with a product; and wherein said step of mounting said slider occurs before said step of attaching said zipper.

63. A method of forming and filling a package, said method comprising;

providing a zipper having one or more spaced primary notches interrupting a portion of said zipper; wherein said zipper includes first and second opposing profiles releasably engageable to each other and a first fin extending downward from said first profile; wherein said zipper includes a second fin extending downward from said second profile; wherein said first fin is detachably connected to said second fin, mounting a slider onto said zipper via a respective one of said primary notches, said slider being adapted to open and close said zipper;

attaching said zipper to a web of thermoplastic film;

forming said zipper-carrying web of film into a package having an open end; and filling said package via said open end with a product.

*64. The method of claim 62, wherein said zipper further includes a plurality of fold areas and a breakable line of weakness or an area of weakness in said fold areas to assist in detaching portions of said zipper.*

* * * * *